US010117901B2

(12) United States Patent
Yoshida et al.

(10) Patent No.: US 10,117,901 B2
(45) Date of Patent: Nov. 6, 2018

(54) PROPHYLACTIC OR THERAPEUTIC AGENT FOR PEPTIC ULCER, FOOD ADDITIVE FOR PROPHYLACTIC OR THERAPEUTIC USE, INOS EXPRESSION INHIBITOR AND COX-2 EXPRESSION INHIBITOR

(71) Applicant: euglena Co., Ltd., Tokyo (JP)

(72) Inventors: Eriko Yoshida, Yokohama (JP); Yuta Asayama, Yokohama (JP); Osamu Iwata, Yokohama (JP); Ayaka Nakashima, Yokohama (JP); Kengo Suzuki, Yokohama (JP); Misa Ohgushi, Sakai (JP); Naoki Harada, Sakai (JP); Yoshihisa Nakano, Sakai (JP)

(73) Assignee: euglena Co., Ltd., Tokyo (JP)

( * ) Notice: Subject to any disclaimer, the term of this patent is extended or adjusted under 35 U.S.C. 154(b) by 0 days.

(21) Appl. No.: 15/524,522

(22) PCT Filed: Nov. 6, 2015

(86) PCT No.: PCT/JP2015/081378
§ 371 (c)(1),
(2) Date: May 4, 2017

(87) PCT Pub. No.: WO2016/072507
PCT Pub. Date: May 12, 2016

(65) Prior Publication Data
US 2017/0319632 A1 Nov. 9, 2017

(30) Foreign Application Priority Data

Nov. 7, 2014 (JP) ................................. 2014-227305
Apr. 8, 2015 (JP) ................................. 2015-079534

(51) Int. Cl.
*A61K 35/68* (2006.01)
*A61K 31/716* (2006.01)

(52) U.S. Cl.
CPC ............ *A61K 35/68* (2013.01); *A61K 31/716* (2013.01)

(58) Field of Classification Search
None
See application file for complete search history.

(56) References Cited

U.S. PATENT DOCUMENTS 5,084,386 A * 1/1992 Tuse .................... A61K 31/715
435/101
2017/0020939 A1 1/2017 Nakashima et al.

FOREIGN PATENT DOCUMENTS

JP 2014-098095 A 5/2014
JP 2014-118374 A 6/2014
WO 2015/156339 A1 10/2015

OTHER PUBLICATIONS

Translation of JP2012051830A. (Year: 2018).*
Translation of JP60196157. (Year: 1985).*
Minako Yoshizawa et al., "Protective Effects of Barley and Its Hydrolysates on Gastric Stress Ulcer in Rats", Yakugaku Zasshi, 2004, pp. 571-575, vol. 124, No. 8.
Wei-Hua Kong et al., "Studies of β-I,3-glucan for Anti Experimental Gastric Ulcer", Journal of Shandong University, 2001, pp. 107-112, vol. 36, No. 1.
Misa Ogushi et al., "Suishin Kosoku Stress ni yoru Ikaiyo ni Taisuru Paramylon Sesshu no Koka", Vitamins, Apr. 25, 2015, pp. 215, vol. 89, No. 4.
'Euglena' no Keizoku Sesshu ga Ikaiyo Shojo o Kanwa—Euglena to Osaka Furitsudai ga Kenkyu Kekka, Nikkan Kogyo Shinbun, Jul. 20, 2015, p. 9.
Euglena Zairyo Fujo, Nippon Shoken Shinbun, Jul. 21, 2015, p. 2.
"Stress Disease Suppressed by Midorimushi Constituent", The Nikkei Business Daily, Jul. 21, 2015, p. 8.
Euglena-sha to Osaka Furitsu Daigaku, euglena Sesshu de Ikaiyo Kanwa o Kakunin, Japan Food Journal, Jul. 24, 2015, p. 6.
Euglena-Osaka Furitsudai, Euglena ga Ikeiyo Kanwa, Dobutsu Jikken de Kakunin, The Chemical Daily, Jul. 28, 2015, p. 4.
Mitchell J. Spirit et al., "Update on Stress Ulcer Prophylaxis in Critically Ill Patients", Critical Care Nurse, Feb. 2006, pp. 18-28, vol. 26, No. 1.
International Search Report for PCT/JP2015/081378, dated Jan. 12, 2016.

* cited by examiner

*Primary Examiner* — Michael Barker
(74) *Attorney, Agent, or Firm* — Sughrue Mion, PLLC

(57) ABSTRACT

Provided are a prophylactic or therapeutic agent for a peptic ulcer, a food additive for prevention and treatment of a peptic ulcer, an iNOS expression inhibitor, and a COX-2 expression inhibitor, all of which have little side effects. The prophylactic or therapeutic agent contains a *Euglena*-derived material as an active ingredient. The *Euglena*-derived material may be *Euglena*, paramylon, or an acid-treated paramylon. The prophylactic or therapeutic agent is useful for the prevention or treatment of a peptic ulcer induced by psychological stress. The peptic ulcer may be a gastric ulcer. The food additive contains a *Euglena*-derived material as an active ingredient.

3 Claims, 7 Drawing Sheets

FIG. 3
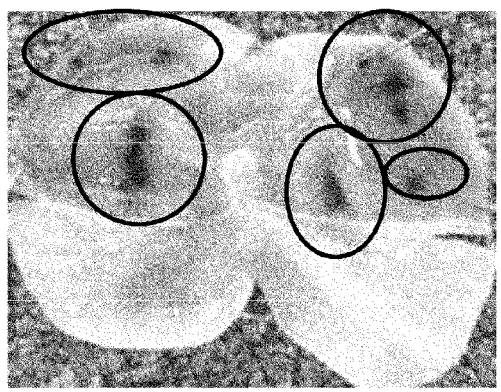
CONTROL GROUP
EUGLENA GROUP
(EX. 1)
PARAMYLON GROUP
(EX. 2)
AMORPHOUS
PARAMYLON GROUP
(EX. 3)

PROPHYLACTIC OR THERAPEUTIC AGENT FOR PEPTIC ULCER, FOOD ADDITIVE FOR PROPHYLACTIC OR THERAPEUTIC USE, INOS EXPRESSION INHIBITOR AND COX-2 EXPRESSION INHIBITOR

CROSS REFERENCE TO RELATED APPLICATIONS

This application is a National Stage of International Application No. PCT/JP2015/081378, filed Nov. 6, 2015, claiming priority based on Japanese Patent Application No. 2014-227305, filed Nov. 7, 2014, and Japanese Patent Application No. 2015-079534, filed Apr. 8, 2015, the contents of all of which are incorporated herein by reference in their entirety.

TECHNICAL FIELD

The present invention relates to a prophylactic or therapeutic agent for a peptic ulcer, a food additive for prevention or treatment of a peptic ulcer, an iNOS expression inhibitor, and a COX-2 expression inhibitor.

BACKGROUND ART

A peptic ulcer refers to a condition in which partially lost epithelia have spread deep inside the mucosal lining of the gastrointestinal tract. Causes of ulcer development are generally considered to be explained based on the balance theory that an ulcer is induced due to a loss of balance between the functions of aggressive factors such as gastric acid, pepsin, stress, *Helicobacter pylori* (hereinafter referred to as "*H. pylori*"), and nonsteroidal anti-inflammatory drugs (hereinafter referred to as "NSAID") and those of protective factors for gastrointestinal mucosa, i.e., mucus and mucosal barriers, blood flow and microcirculation, growth factors, and prostaglandin.

Major peptic ulcers include gastric ulcers and duodenal ulcers.

Gastric ulcers are caused mainly by weakened defense mechanisms for gastric mucosa. Infection with *H. pylori*, NSAID, and stress weaken the defense mechanisms to cause damage to gastric mucosa, which progresses into an ulcer. Duodenal ulcers are caused by increased secretion of gastric acid, which causes damage to duodenal mucosa, which is vulnerable to attack by gastric acid. Infection with *H. pylori* also weakens duodenal mucosa. High-fat diets and the like lead to increased secretion of gastric acid.

The three most common causes of gastric and duodenal ulcers are infection with *H. pylori*, nonsteroidal anti-inflammatory drugs (NSAID), and stress.

Among these causes, stress such as social stress may result in a stress-induced ulcer, which is mainly caused by psychological stress. It is desirable to develop a prophylactic drug for stress-induced ulcers, the drug capable of being administered, in daily living, to those in an environment where they are susceptible to psychological stress and those prone to have psychological stress without side effects.

It is also desirable to develop prophylactic and therapeutic agents that can be used for a peptic ulcer caused by *H. pylori* or NSAID rather than psychological stress and that have no side effects.

It has been reported that if a patient in an intensive care unit has two risk factors: controlled artificial respiration for 48 hours or longer and a clotting disorder, the patient has an increased risk for clinically-significant gastrointestinal bleeding and has increased mortality. Thus, if a patient in an intensive care unit has these two risk factors, a PPI (proton pump inhibitor) or an $H_2RA$ (histamine 2 receptor antagonist) for prevention of a stress-induced gastrointestinal ulcer is typically administered to provide preventive treatment of a stress-induced ulcer and bleeding (for example, Non Patent Literature 1).

CITATION LIST

Non Patent Literature

Non Patent Literature 1: Mitchell J. Spirt et al., "Update on Stress Ulcer Prophylaxis in Critically Ill Patients," [online], Crit Care Nurse 2006, 26:18-28. [retrieved on Jun. 24, 2014], and the internet (http://ccn.aacnjournals.org/content/26/1/18.full.pdf+html)

SUMMARY OF INVENTION

Technical Problem

However, it has been reported that when patients do not receive enteral nutrition, gastrointestinal bleeding is significantly inhibited in an $H_2RA$-treated group, while when patients receive enteral nutrition, not only the effect of the $H_2RA$ in the prevention of gastrointestinal bleeding disappears, but the risk of pneumonia is increased in an $H_2RA$-treated group (Crit Care 2012; 16: 322).

Although PPI are more recommended than $H_2RA$, PPI are potent gastric-acid anti-secretory agents. Thus, PPI have been reported to be associated with an increased risk of gastric cancer (Br. J. Cancer, 100, 1503-1507 (2009)) and pneumonia (JAMA, 301, 2120-2128(2009)) and are expected to be associated with an increased risk of bone fracture and enteric infections.

Despite the fact that conventional anti-ulcer drugs have side effects and that patients in an intensive care unit have a risk for a stress-induced ulcer and bleeding, doctors have been compelled to rather hesitantly offer preventive treatment for a peptic ulcer to patients in an intensive care unit.

It was believed that psychological stress such as anxiety or fear alone is less likely to cause a gastric or duodenal ulcer. However, a study through addition of the incidents of a peptic ulcer before and after a recent earthquake disaster has confirmed that peptic ulcers and non-*H. pylori* and non-NSAID ulcers were increased during the three months after the earthquake disaster, compared with the same period in the preceding year, whereby indicating that psychological stress alone can induce a peptic ulcer (J Gastroenterol. 2013 April; 48(4): 483-90. doi: 10.1007/s00535-012-0681-1. Epub 2012 Oct. 3).

Upon occurrence of a natural disaster, large-scale fires, an accident or a crime, or during a war, many casualties, victims, supporters, and the like are exposed to psychological stress and have an increased risk of a stress-induced ulcer associated with the psychological stress. Under such a situation, doctors are limited relative to casualties and the like, and thus it is difficult in practice to continuously administer a PPI, $H_2RA$, or the like, which has strong side effects, simultaneously to many victims and the like to prevent a stress-induced ulcer.

The present invention has been developed in view of the foregoing. Objects of the present invention are to provide a prophylactic or therapeutic agent for a peptic ulcer, a food additive for prevention and treatment of a peptic ulcer, an iNOS expression inhibitor, and a COX-2 expression inhibitor, all of which have little side effects.

Solution to Problem

According to the present invention, the above problem is solved by a prophylactic or therapeutic agent for a peptic ulcer, the agent containing a *Euglena*-derived material as an active ingredient.

The prophylactic or therapeutic agent for a peptic ulcer according to the present invention contains, as an active ingredient, a *Euglena*-derived material with no side effects reported yet and with safety generally conforming to the Japanese Food Sanitation Act. Thus, unlike conventional prophylactic or therapeutic agents for a peptic ulcer, the prophylactic or therapeutic agent of the invention has no side effects and can be continuously administered for a long period of time.

Then, the prophylactic or therapeutic agent of the present invention can be continuously administered to those having social and psychological stress for preventive or therapeutic purposes.

The prophylactic or therapeutic agent of the present invention can be suitably used as a prophylactic drug for a peptic ulcer, the drug being recommended for use in intensive care units. As no side effects have been reported, the prophylactic or therapeutic agent of the present invention does not require very cautious administration to a patient in an intensive care unit, unlike conventional prophylactic drugs for a peptic ulcer.

The *Euglena*-derived material may be *Euglena*, paramylon, or an acid-treated paramylon.

Such configuration allows to bring about prophylactic or therapeutic effects for the prevention and treatment of a peptic ulcer without side effects.

Especially when *Euglena* is used as the *Euglena*-derived material, various nutrients such as vitamins, amino acids, and fatty acids that are contained in the *Euglena* can also be administered to an individual or a patient, thereby improving the nutritional status of the individual or the patient in parallel.

Thus, for example, when the agent of the present invention is administered to a patient in an intensive care unit as a prophylactic agent for a peptic ulcer, the agent can provide the effect of preventing a peptic ulcer and can also improve the nutritional status to promote the restoration of his or her strength.

The peptic ulcer to be prevented or treated may be one associated with psychological stress.

The peptic ulcer may also be a gastric ulcer.

According to the present invention, the above problem can also be solved by a food additive for prevention or treatment of a peptic ulcer, the additive containing a *Euglena*-derived material as an active ingredient.

The food additive of the present invention contains, as an active ingredient, a *Euglena*-derived material with no side effects reported yet and with safety generally conforming to the Japanese Food Sanitation Act. Thus, unlike conventional prophylactic or therapeutic agents for a peptic ulcer, the food additive of the present invention has no side effects and can be continuously administered for a long period of time.

Then, the food additive of the present invention can be continuously administered to individuals or patients having social and psychological stress for preventive or therapeutic purposes.

For example, in a situation such that many people simultaneously have psychological stress after an earthquake or the like, many of them can be prevented or inhibited from developing a peptic ulcer without a doctor's prescription, by providing disaster sufferers, supporters, and the like with food or the like that contains the food additive of the present invention for prevention or treatment of a peptic ulcer.

The above problem can also be solved by an iNOS (inducible nitric oxide synthase) expression inhibitor according to the present invention, the inhibitor containing a *Euglena*-derived material as an active ingredient.

As the iNOS expression inhibitor contains, as an active ingredient, a *Euglena*-derived material, which has the effect of inhibiting expression of iNOS that leads to excessive inflammation, the iNOS expression inhibitor can inhibit a peptic ulcer by reducing oxidative damage due to stress.

The above problem can also be solved by a COX-2 expression inhibitor according to the present invention, the inhibitor containing a *Euglena*-derived material as an active ingredient.

As the COX-2 expression inhibitor contains, as an active ingredient, a *Euglena*-derived material, which has the effect of inhibiting expression of COX-2, as described above, the COX-2 expression inhibitor can inhibit a peptic ulcer by reducing oxidative damage due to stress through inhibition of expression of COX-2, which is a rate-limiting enzyme in the biosynthesis of prostaglandin that leads to excessive inflammation.

The above problem can also be solved by a stress suppressor according to the present invention, the suppressor containing a *Euglena*-derived material as an active ingredient and suppressing stimulation induced by stress in a living body.

As the stress suppressor of the present invention contains, as an active ingredient, a *Euglena*-derived material which has the effect of inhibiting expression of iNOS and COX-2, the stress suppressor can suppress stimulation in a living body induced by stress such as stress due to biochemical substances such as prostaglandin and reactive oxygen. Thus, the stress suppressor can inhibit a peptic ulcer by reducing cell damage such as oxidative injury caused by stimulation with stress.

Advantageous Effects of Invention

The prophylactic or therapeutic agent for a peptic ulcer according to the present invention contains, as an active ingredient, a *Euglena*-derived material with no side effects reported yet and with safety generally conforming to the Japanese Food Sanitation Act. Thus, unlike conventional prophylactic or therapeutic agents for a peptic ulcer, the agent according to the present invention has no side effects and can be continuously administered for a long period of time.

Then, the prophylactic or therapeutic agent of the present invention can be continuously administered to those having social and psychological stress for preventive or therapeutic purposes.

BRIEF DESCRIPTION OF DRAWINGS

FIG. 3 shows photographs illustrating gastric ulcers as representative examples in the respective groups in Test 1.

DESCRIPTION OF EMBODIMENTS

Figure 1:
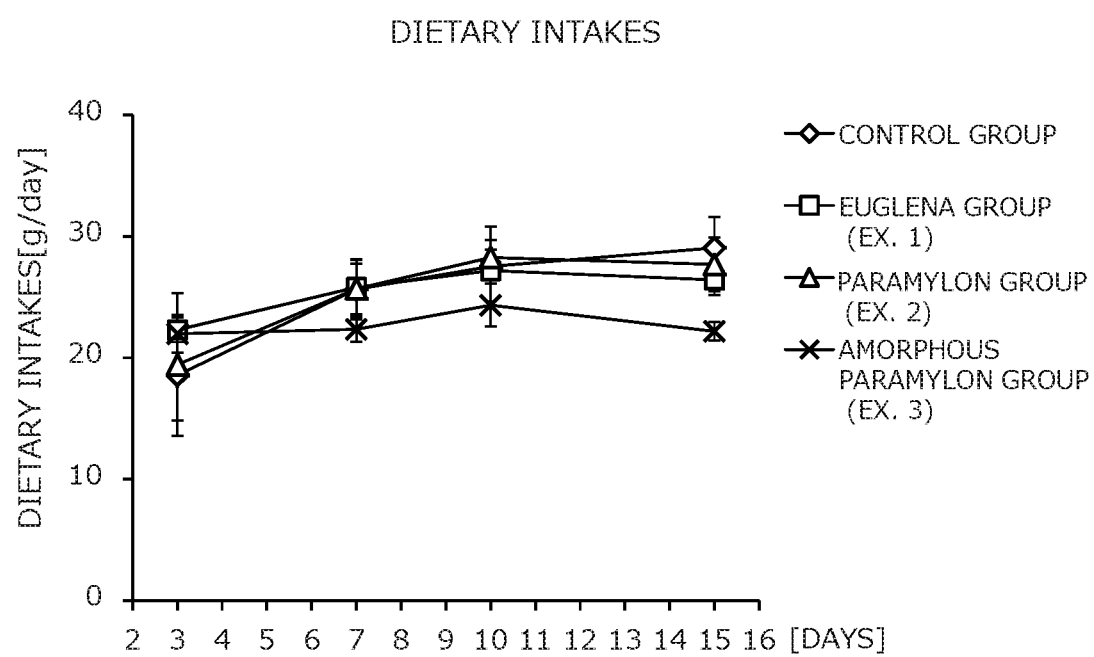
FIG. 1 is a graph illustrating dietary intakes by rats of respective groups for 14 days in Test 1.

Now, a prophylactic or therapeutic agent for a peptic ulcer and a food additive for prevention and treatment of a peptic ulcer, both of which are according to embodiments of the present invention, will be described with reference to FIGS. 1-7.

<Peptic Ulcers>

A peptic ulcer refers to a condition in which partially lost epithelia have spread deep inside the mucosal lining of the gastrointestinal tract. Particularly, peptic ulcers mean those which occur in the gastrointestinal tract due to attack of gastric acid, pepsin, psychological stress, *H. pylori*, NSAID, or the like.

Peptic ulcers include upper gastrointestinal ulcers, which occur in the esophagus, stomach, and duodenum, and lower gastrointestinal ulcers, which occur in the small intestine and colon. The peptic ulcers also encompass peptic ulcers after removal of *H. pylori*, reflux esophagitis, gastroesophageal reflux disease, and the like.

<Prophylactic or Therapeutic Agent for Peptic Ulcer>

The prophylactic or therapeutic agent of the embodiment contains a *Euglena*-derived material.

Suitable examples of the *Euglena*-derived material include *Euglena*, dried *Euglena*, paramylon, and processed products from paramylon.

*Euglena* have been attracting attention as a bioresource that is promising for use as food, feed, fuel, and the like.

*Euglena* contains as many as 59 nutrients such as vitamins, minerals, amino acids, and unsaturated fatty acids, which represent the majority of the essential nutrients for humans. Studies have demonstrated the feasibility of using *Euglena* as supplements that provide a balanced combination of various types of nutrients and also as a food supply source in poor regions where people cannot take necessary nutrients. Antioxidants are included in the 59 nutrients.

*Euglena* are in the bottom of the food chain and are eaten by animals. It is more difficult to identify conditions for cultivating *Euglena*, such as light, temperature, and agitation speed, compared with other microorganisms. Thus, it has been considered difficult to mass cultivate *Euglena*. In recent years, however, the inventors of the present invention have developed a technique for the mass cultivation of *Euglena* through their extensive research and have paved the way for a large supply of paramylon.

*Euglena* are unique living organisms that have animal features such as flagellar motility and also have chloroplast and photosynthesize just like a plant. It is expected that *Euglena* themselves and *Euglena*-derived materials have many functionalities.

As *Euglena* cells, *Euglena gracilis* (*E. gracilis*) and, in particular, the strain *Euglena gracilis* (*E. gracilis*) Z can be used. The *Euglena* may also be species such as *Euglena gracilis* Klebs, *Euglena gracilis* var. *bacillaris*, the strain SM-ZK (chloroplast deficient strain), which is a mutant derived from the strain *Euglena gracilis* (*E. gracilis*) Z, var. *bacillaris*, or β-1,3-glucanase derived from a genetic mutant strain such as chloroplast mutants thereof, *Euglena intermedia, Euglena piride*, and other *Euglena* such as, for example, *Astaia longa*.

*Euglena* generally live in fresh water such as pools and ponds, and thus *Euglena* may be isolated from such water. Alternatively, any previously-isolated *Euglena* may be used.

The *Euglena* in the present invention encompass all mutant strains. The mutant strains encompass those produced through genetic techniques such as, for example, recombination, transduction, and transformation.

Culture for cultivating *Euglena* cells may be, for example, culture supplemented with nutrient salts such as one or more nitrogen sources, phosphorus sources, and minerals. For example, modified Cramer-Myers medium (1.0 g/L of $(NH_4)_2HPO_4$, 1.0 g/L of $KH_2PO_4$, 0.2 g/L of $MgSO_4.7H_2O$, 0.02 g/L of $CaCl_2.2H_2O$, 3 mg/L of $Fe_2(SO_2)_3.7H_2O$, 1.8 mg/L of $MnCl_2.4H_2O$, 1.5 mg/L of $CoSO_4.7H_2O$, 0.4 mg/L of $ZnSO_4.7H_2O$, 0.2 mg/L of $Na_2MoO_4.2H_2O$, 0.02 g/L of $CuSO_4.5H_2O$, 0.1 mg/L of thiamine hydrochloride (vitamin $B_1$), cyanocobalamin (vitamin $B_{12}$), (pH 3.5)) can be used. The $(NH_4)_2HPO_4$ may be replaced by $(NH_4)_2SO_4$ or $NH_3$aq. Known Hutner medium or Koren-Hutner medium prepared according to the description in "*Euglena*—Physiology and Biochemistry (in Japanese)" (Kitaoka, S (ed.), Gakkai Shuppan Center, K.K.) may also be used.

The culture preferably has a pH of 2 or higher, preferably with an upper limit being 6 or lower, and more preferably with an upper limit being 4.5 or lower. In the culture having an acidic pH, photosynthetic microorganisms can grow better than other microorganisms, so that contamination can be suppressed.

*Euglena* cells may be cultivated using an open pond process that directly uses sun light, or a light collection method that collects sunlight through a light collection device, which is subsequently transmitted through fiber optics or the like to a fermenter tank where the cells are exposed to the light for photosynthesis.

*Euglena* cells may also be cultivated using, for example, a fed-batch process. *Euglena* cells may be cultivated using any liquid cultivation process such as flask cultivation, fermenter cultivation, batch cultivation, semi-batch cultivation (fed-batch cultivation), or continuous cultivation (perfusion cultivation).

*Euglena* cells can be cultivated using a known fermenter such as an open pond fermenter, a raceway fermenter, or a tubular fermenter or a laboratory fermenter such as a Sakaguchi flask, an Erlenmeyer flask, or a reagent bottle. *Euglena* utilize $CO_2$, and thus if *Euglena* is cultivated using the Cramer-Myers medium, which is an autotrophic medium, the medium is preferably gassed with air containing 1-5% $CO_2$. It is also preferred to add about 1-5 g of ammonium phosphate per liter of the medium to sufficiently develop chloroplasts. Suitably, the cultivation is carried out generally at a temperature of from 20 to 34° C. and particularly from 28 to 30° C. *Euglena* usually enter the logarithmic growth phase in 2-3 days after the initiation of the cultivation and reach the stationary phase in 4-5 days, depending on the cultivation conditions.

*Euglena* may be cultivated under light exposure (light cultivation) or without light exposure (dark cultivation).

*Euglena* cells may be isolated by, for example, centrifugation of the culture, simple sedimentation, or membrane filtration.

The dried *Euglena* is prepared by washing isolated *Euglena* cells and then vacuum freeze-drying the cells by a known method. Alternatively, the dried *Euglena* may be prepared by spray drying, vacuum heat-drying, or the like.

Paramylon is a polymer of about 700 glucose units polymerized through β-1,3-linkages (β-1,3-glucan) and is a reserve polysaccharide contained in *Euglena*. Paramylon particles have a flattened spheroid shape and are formed of entangled helical β-1,3-glucan chains.

Paramylon exists, as granules, in *Euglena* cells of all species and varieties, and the number, shape, and particle uniformity vary with the species.

Paramylon is composed of glucose only, and paramylon from wild type *E. gracilis* Z or chloroplast deficient mutant SM-ZK has an average degree of polymerization of about 700 glucose units.

While paramylon is insoluble in water and hot water, paramylon is soluble in dilute alkali, concentrated acid, dimethyl sulfoxide, formaldehyde, and formic acid.

Paramylon in *E. gracilis* Z and paramylon in *E. gracilis* var. *bacillaris* SM-L1 have average densities of 1.53 and 1.63, respectively.

X-ray analysis using a powder pattern technique shows that paramylon assumes a gentle helical configuration of three linear β-glucan chains twined together like a right-hand rope. Some of the glucan molecules aggregate to form each paramylon granule. Paramylon granules have a large number of crystal structures, which make up about 90%, and paramylon is a compound having the highest crystal structure ratio among polysaccharides. Paramylon is also less likely to contain water ("*Euglena*-Physiology and Biochemistry (in Japanese)" (Kitaoka, S (ed.), Gakkai Shuppan Center, K.K.)).

Paramylon (from *Euglena* Co., Ltd.) has a median size as a particle size distribution of 1.5-2.5 μm, as measured on a laser diffraction/scattering particle size distribution analyzer.

Paramylon particles are isolated from cultivated *Euglena* by any suitable technique and are purified into fine particles, which are usually provided as powder.

For example, paramylon particles can be obtained by (1) cultivation of *Euglena* cells in any suitable medium, (2) separation of the *Euglena* cells from the medium, (3) isolation of paramylon from the separated *Euglena* cells, (4) purification of the isolated paramylon, and optionally, (5) cooling and subsequent freeze-drying.

Paramylon may be isolated using, for example, a nonionic or anionic surfactant of a type that it is mostly biodegradable. In practice, paramylon can be purified simultaneously with its isolation.

Isolation and purification of paramylon from *Euglena* are well known and described in, for example, E. Ziegler, "Die naturlichen and kunstlichen Aromen" Heidelberg, Germany, 1982, Chapter 4.3 "Gefriertrocken", DE 43 28 329, and JP 2003529538A.

Examples of the processed product from paramylon include amorphous paramylon prepared by treating, with acid, crystalline paramylon derived from *Euglena* and then gelling the treated product with alkali to amorphize the crystalline paramylon.

Amorphous paramylon used in the subsequent embodiment has a relative crystallinity of 1-20% relative to that of crystalline paramylon produced from *Euglena* by a known method.

The relative crystallinity is determined by the method described in Japanese Patent Application No. 2010-52042.

In particular, amorphous paramylon and paramylon are individually ground in a pulverizer (MM400 ball mill from Retsh) at 20 oscillations per second for 5 minutes, and then scanned with an X-ray diffractometer (H'PertPRO from Spectris Co., Ltd.) at a tube voltage of 45 KV, a tube current of 40 mA, and 2θ in the range of from 5° to 30° to obtain diffraction peaks Pc for the paramylon and Pa for the amorphous paramylon at 2θ of about 20°.

The Pc and Pa values are used to calculate the relative crystallinity of amorphous paramylon as follows:

Relative Crystallinity of Amorphous Paramylon=$Pa/Pc \times 100 (\%)$

Amorphous paramylon used in the embodiment is prepared by treating crystalline paramylon powder with alkali, neutralizing the treated product with acid, washing the product, processing the washed product through a water removing step, and then drying the product in accordance with the method described in JP5612875B.

Processed products from paramylon additionally include water-soluble paramylon, sulfated paramylon, and the like that are obtained by chemically or physically treating paramylon by various other known methods, and paramylon derivatives.

The prophylactic or therapeutic agent of the embodiment can be used as a prophylactic or therapeutic agent or drug for a peptic ulcer.

The prophylactic agent or drug can be administered to those at high risk for developing a peptic ulcer such as, for example, those having psychological stress, those after completion of treatment of their peptic ulcer, those after completion of removal of *H. pylori*, and those after failure to remove *H. pylori*.

The prophylactic agent or drug is applicable to pre-ulcer conditions such as, for example, inflammation of the gastrointestinal tract and conditions including chest discomfort, abdominal discomfort, upset stomach, and abdominal bloating due to injury to the mucosa of gastrointestinal tracts such as esophagus, stomach, duodenum, and small intestine.

The prophylactic or therapeutic agent of the embodiment contains, as an active ingredient, *Euglena*, paramylon, or an acid-treated paramylon conforming to the standards of the Japanese Food Sanitation Act and the like. *Euglena*, paramylon, or the acid-treated paramylon is sufficiently safe to be regularly eaten as food, and no side effects have been reported yet.

Thus, when a therapeutically effective amount of the prophylactic or therapeutic agent of the embodiment is administered, as a medicament, to an individual before developing a peptic ulcer or a patient having a peptic ulcer, the prophylactic or therapeutic agent does not cause any side effects beyond a medically acceptable level.

Thus, the prophylactic agent of the embodiment can be continuously administered for a long period to those in an environment where they are susceptible to psychological and social stress, such as, for example, those who work or live in an environment where they are susceptible to mental stress and those who are preparing for a test or the like.

As those after completion of treatment of their peptic ulcer are likely to suffer peptic ulcer relapse, the prophylactic agent of the embodiment can be continuously administered to them for the prevention and inhibition of peptic ulcer relapse.

In addition, the prophylactic agent of the embodiment can be administered to patients for whom prevention or treatment of a peptic ulcer is recommended, such as patients in an intensive care unit who have two risk factors: controlled artificial respiration for 48 hours or longer and a clotting disorder. Among these patients, the prophylactic agent is particularly suitable for use as a prophylactic agent for prevention of a peptic ulcer in patients after initiation of enteral nutrition.

Conventionally, agents such as PPI and H₂RA that have side effects such as pneumonia have been administered to patients in an intensive care unit for whom prevention or treatment of a peptic ulcer is recommended, and such administration may cause serious side effects on patients who are already in a serious condition and who are physically weak. In contrast, the prophylactic drug of the embodiment does not cause any side effect beyond a medically acceptable level and thus does not require very cautious administration even when the drug is administered to a patient in an intensive care unit to prevent or treat a peptic ulcer, unlike the conventional agents.

When the prophylactic agent with *Euglena* or dried *Euglena* contained as an active ingredient therein is used as a prophylactic agent for a peptic ulcer, about 60 nutrients contained in the *Euglena*, including vitamins, minerals, amino acids, and unsaturated fatty acids, can also be administered to a patient, so that a patient in an intensive care unit, who is physically feeble, is allowed to restore his or her strength. Especially for a patient after initiation of enteral nutrition, the prophylactic agent can promote the intake of nourishment.

The prophylactic or therapeutic agent of the embodiment allows for provision of a pharmaceutical composition that has the effect of preventing and treating a peptic ulcer by formulating a *Euglena*-derived material in an amount sufficient to effectively provide the effect of preventing or treating a peptic ulcer, with a pharmaceutically acceptable carrier and a pharmaceutically acceptable additive. The pharmaceutical composition may be a pharmaceutical drug or a quasi-drug.

The pharmaceutical composition may be used internally or externally. In particular, the pharmaceutical composition may be used in a dosage form such as an oral agent; an injectable such as an intravenous injectable, a subcutaneous injectable, an intradermal injectable, an intramuscular injectable, and/or an intraperitoneal injectable; a transmucosal agent; or a transdermal agent.

The dosage form of the pharmaceutical composition can be appropriately determined depending on the administration mode, and examples include solid formulations such as tablets, granules, capsules, and powders; and fluid formulations such as solutions and suspensions; and semi-solid formulations such as ointments and gels.

The therapeutic agent or drug of the embodiment can be administered alone or in combination with another drug for peptic ulcer, such as PPI and H₂RA, to a patient having a peptic ulcer.

To those with a body weight of from 40 to 90 kg, the prophylactic or therapeutic agent of the embodiment is administered in an amount so that *Euglena* powder, paramylon powder, or powder of a processed product from paramylon is given at a dose of 0.05 g or more and preferably 1 g or more per day.

As the prophylactic or therapeutic agent of the embodiment produces a beneficial effect about 90 days after initiation of administration, it is preferable to administer the agent for 100-300 days.

The prophylactic or therapeutic agent of the embodiment inhibits the expression of iNOS (inducible nitric oxide synthase) and COX-2 (inducible cyclooxygenase) in a living body, thereby reducing oxidative damage due to stimulation of a living body by stress to inhibit a peptic ulcer.

Stimulation of a living body by stress refers to stimulation with external stress (stressor) due to psychological stress, and the stimulation, as used herein, includes stress due to biochemical substances and more particularly oxidative stress. Living bodies induce a stress response to the stimulation with stress.

<Food Additive for Prevention or Treatment of Peptic Ulcer>

The food additive of the embodiment for prevention of a peptic ulcer may be given to those at high risk for developing a peptic ulcer, such as, for example, those having psychological stress, those after completion of treatment of their peptic ulcer, those after completion of removal of *H. pylori*, and those after failure to remove *H. pylori*.

The food additive for prevention of the peptic ulcer is applicable to pre-ulcer conditions such as, for example, inflammation of the gastrointestinal tract and conditions including chest discomfort, abdominal discomfort, upset stomach, and abdominal bloating due to injury to the mucosa of the gastrointestinal tract such as esophagus, stomach, duodenum, and small intestine.

The food additive of the embodiment for treatment of the peptic ulcer can be given alone or in combination with another drug for the peptic ulcer such as PPI and H₂RA, to a patient having a peptic ulcer.

The food additive of the embodiment contains, as an active ingredient, *Euglena*, paramylon, or an acid-treated paramylon conforming to the standards of the Japanese Food Sanitation Act and the like. *Euglena*, paramylon, or the acid-treated paramylon is sufficiently safe to be regularly eaten as food, and no side effects have been reported yet.

Thus, when a prophylactically or therapeutically effective amount of the food additive of the embodiment is given to an individual before developing a peptic ulcer or a patient having a peptic ulcer, the food additive agent does not cause any side effect beyond a medically acceptable level.

Thus, the food additive of the embodiment can be continuously given for a long period.

In a situation such that many people simultaneously have psychological stress for a certain period of time, including, for example, a natural disaster such as a big earthquake or tsunami, a large-scale terrorist attack, a crime, widespread fires, a large-scale accident, or a pandemic of an infection, food that contains the food additive of the embodiment can be provided for disaster sufferers, victims, casualties, supporters, and the like in the relevant area, in an amount sufficient to allow them to take the food additive for a predetermined period of time, so that they can take the food additive themselves.

The food additive of the embodiment is not a medicament and thus does not require a doctor's prescription, which allows people to take the additive themselves even when physicians are not sufficiently available in a large-scale disaster or the like. Thus, many disaster sufferers and the like can be efficiently prevented from developing a peptic ulcer induced by psychological stress.

The food additive of the embodiment allows various food to be formulated with a *Euglena*-derived material as a food material in an amount sufficient to exhibit prophylactic or therapeutic effects for a peptic ulcer in a living body, thereby providing a food composition that has the effect of preventing or treating a peptic ulcer. In other words, the present invention can provide, in the field of food, food compositions having an indication that they are useful for the prevention or treatment of peptic ulcer. Examples of these food compositions include general food, food for specified health use, nutritional supplement food, functional food, food for inpatients, and supplements. The composition may also be used as a food additive.

As used herein, "food for specified health use" refers to food that contains a healthy component having an effect on a physiological function or the like and that has gained approval from the Secretary General of the Japanese Consumer Affairs Agency to indicate that the food is suitable for specified health use.

"Food with nutrient function claims" refers to food that is used to supplement the diet with a nutrient component (vitamin or mineral) and that is provided with an indication of the function of the nutrient component. To sell a food product as food with nutrient function claims, the food product must satisfy the standard for the minimum and maximum levels of the nutrient component per daily portion usually consumed and must be labelled with not only a nutrient function, but also warning.

"Food with function claims" refers to food that is labelled with a function based on scientific evidence under the responsibility of an entity. Prior to marketing the food product, the entity must provide information or the like on evidences for safety and function to the Secretary General of the Japanese Consumer Affairs Agency.

Examples of the food compositions can include seasoning, processed meat products, processed agricultural products, drinks (such as soft drinks, alcoholic drinks, carbonated drinks, milk drinks, fruit drinks, teas, coffee, and nourishing drinks), powdered drinks (such as powdered juice and powdered soup), concentrated drinks, confectionery (such as candies, cookies, crackers, gums, gummi candies, and chocolates), bread, and cereals. In the case of food for specified health use, nutritional supplement food, functional food, or the like, the compositions may each be in the form of capsules, troches, syrup, granules, powder, or the like.

<Others>

The prophylactic or therapeutic agent of the embodiment can be used to apply a *Euglena*-derived material for the manufacture of a pharmaceutical drug for inhibiting a peptic ulcer.

In addition, the prophylactic or therapeutic agent of the embodiment can be used in a method for preventing or treating a peptic ulcer, the method including administering an effective amount of the *Euglena*-derived material or allowing a subject to take an effective amount of the *Euglena*-derived material.

EXAMPLES

Now, the present invention will be described in more detail with reference to specific examples, although the present invention is not limited to the following examples.

Samples of the following Examples 1-3 were prepared, and their pharmacological actions in gastric ulcer models were studied in the following Study Example 1.

Example 1

*Euglena gracilis* powder (from *Euglena* Co., Ltd.) was used as *Euglena* of Example 1.

Example 2

Crystalline paramylon was prepared in the following manner.

The *Euglena gracilis* powder of Example 1 (from *Euglena* Co., Ltd.) was added to distilled water and stirred at room temperature for 2 days. The resultant was ultrasonically treated to destroy the cell membranes, and crude paramylon particles were collected by centrifugation. The collected paramylon particles were dispersed in a 1% aqueous solution of sodium dodecyl sulfate and treated at 95° C. for 2 hours. After the paramylon particles were collected by centrifugation again, the paramylon particles were dispersed in a 0.1% aqueous solution of sodium dodecyl sulfate and treated at 50° C. for 30 minutes. Lipids and proteins were removed by those operations. Then, the remainder was washed with acetone and ether and dried at 50° C. to give purified paramylon particles.

The prepared paramylon was used as paramylon of Example 2.

Example 3

The paramylon prepared in Example 2 was used to prepare amorphous paramylon in accordance with the method described in Japanese Patent Application No. 2010-52042.

Specifically, the crystalline paramylon powder prepared in Example 2 was added to and dissolved in 1 N aqueous sodium hydroxide at a concentration of 5% (w/v) and stirred for 1-2 hours with a stirrer for alkali treatment. Then, 1 N hydrochloric acid was added dropwise to the solution of the paramylon powder in the 1 N aqueous sodium hydroxide to neutralize the solution. After centrifugation, the supernatant was removed, and the precipitate was washed with distilled water. After these operations were repeated, the precipitated gel was collected. After freezing, the gel was freeze-dried using a lyophilizer to give amorphous paramylon of Example 3.

(Test 1: Verification of Pharmacological Actions in Gastric Ulcer Models)

In a water immersion stress test in rats, the *Euglena* of Example 1, the paramylon of Example 2, and the amorphous paramylon of Example 3 were administered, and inhibition effects of the active ingredients of Examples 1-3 on a gastric ulcer were tested for verification.

Six (6) week old male rats (Wistar) were pre-conditioned on a conditioning diet (CLEA Rodent Diet CE-2, CLEA Japan, Inc.) for 4 days prior to the initiation of the test, and then rats of a control group and an Example 1 *Euglena* group, an Example 2 paramylon group, an Example 3 amorphous paramylon group were fed on the respective diets described in Table 1 for 14 days.

In Table 1, the diet for the Example 1 group was prepared by reducing the amounts of the respective ingredients of the diet for the control group to 97% and adding the *Euglena* in an amount of 3% based on the total weight. The diets for the Example 2 and 3 groups were each prepared by reducing the amount of cellulose in the diet for the control group by 3% and adding paramylon or amorphous paramylon in an amount of 3%. As paramylon and amorphous paramylon are a glucan, they can nutritionally substitute for cellulose. In contrast, as *Euglena* contains not only the glucan, but also various nutrients, *Euglena* substituted for 3% of the respective ingredients.

Thus, the diets for the respective groups had an energy ratio and an energy density of the three major nutrients as illustrated in Table 2 and had the substantially same nutrient balance.

Figure 2:
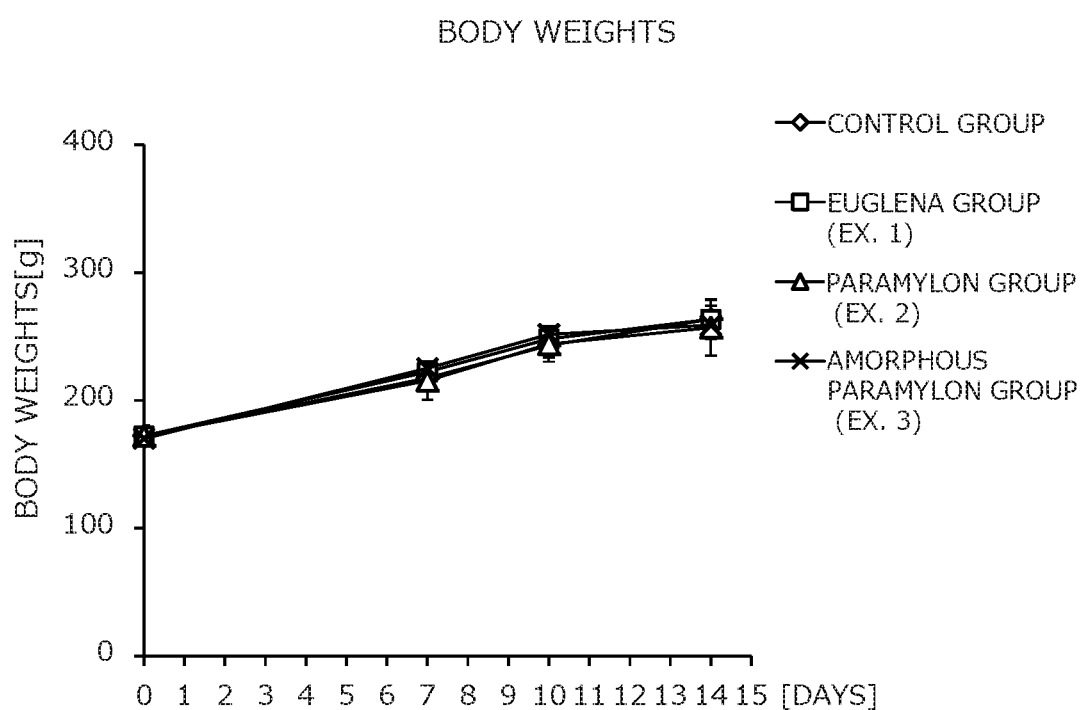
FIG. 2 is a graph illustrating the body weights of rats of the respective groups that were allowed to take the corresponding diets for 14 days in Test 1.

The dietary intakes by the rats of the respective groups for 14 days are illustrated in FIG. 1, and the body weights are illustrated in FIG. 2.

TABLE 1

| Composition (%) | Control Group | Euglena Group (Example 1) | Paramylon Group (Example 2) | Amorphous Paramylon Group (Example 3) |
|---|---|---|---|---|
| Casein | 14.0 | 13.6 | 14.0 | 14.0 |
| L-cystine | 0.18 | 0.17 | 0.18 | 0.18 |
| β-cornstarch | 46.6 | 45.2 | 46.6 | 46.6 |
| α-cornstarch | 15.5 | 15.0 | 15.5 | 15.5 |
| Sucrose | 10.0 | 9.7 | 10.0 | 10.0 |
| Soybean Oil | 4.0 | 3.9 | 4.0 | 4.0 |
| Cellulose | 5.0 | 4.9 | 2.0 | 2.0 |
| Mineral Mix (AIN-93M-MX) | 3.5 | 3.4 | 3.5 | 3.5 |
| Vitamin Mix (AIN-93V-MX) | 1.0 | 1.0 | 1.0 | 1.0 |
| Choline Bitartrate | 0.25 | 0.24 | 0.25 | 0.25 |
| TBHQ | 0.0008 | 0.0008 | 0.0008 | 0.0008 |
| Sample of Example 1, 2, or 3 | 0 | 3 | 3 | 3 |
| Total (%) | 100 | 100 | 100 | 100 |

TABLE 2

| Total Energy (%) | Control Group | Euglena Group (Example 1) | Paramylon Group (Example 2) | Amorphous Paramylon Group (Example 3) |
|---|---|---|---|---|
| Protein | 0.49 | 0.55 | 0.49 | 0.49 |
| Carbohydrate | 2.61 | 2.55 | 2.61 | 2.61 |
| Fat | 0.42 | 0.41 | 0.42 | 0.42 |
| Energy (kcal/g diet) | 3.52 | 3.51 | 3.52 | 3.52 |

The rats of each of the groups were given the corresponding diet described in Table 1 for 14 days and then were fasted overnight.

Then, the rats of each of the groups were restrained in a stress cage and immersed for 18 hours in water to chest level. Then, the rats were dissected to examine a gastric ulcer.

After each rat of each of the groups was weighed, the kidneys, spleen, duodenum, and epididymal adipose tissues of the rat of the group were removed and weighed, and the weights of the respective organs were compared with the body weight of the rat to determine the relative weights. Then, a comparison of the results with the weights of the control group indicated that the organs except for the duodenum exhibited no change especially in relative weight. In contrast, only the duodenums in Examples 1 and 2 exhibited a significant increase (p<0.05 by Tukey-Kramer test). Thus, it is expected that the present invention provides the effect of growing digestive organs. The relative weights of the duodenums are illustrated in Table 3.

TABLE 3

| Relative Weight (g %) | Diet Group | | | |
|---|---|---|---|---|
| | Control Group | Euglena Group (Example 1) | Paramylon Group (Example 2) | Amorphous Paramylon Group (Example 3) |
| Duodenums | 0.085 ± 0.0052[a] | 0.110 ± 0.0054[b] | 0.118 ± 0.0063[b] | 0.100 ± 0.0096[a] |

Mean ± S.D. (g %)
[a,b]p < 0.05

Stomachs of the rats of each of the groups were removed, and ulcers in the mucosal surfaces were photographed and measured.

Figure 4:
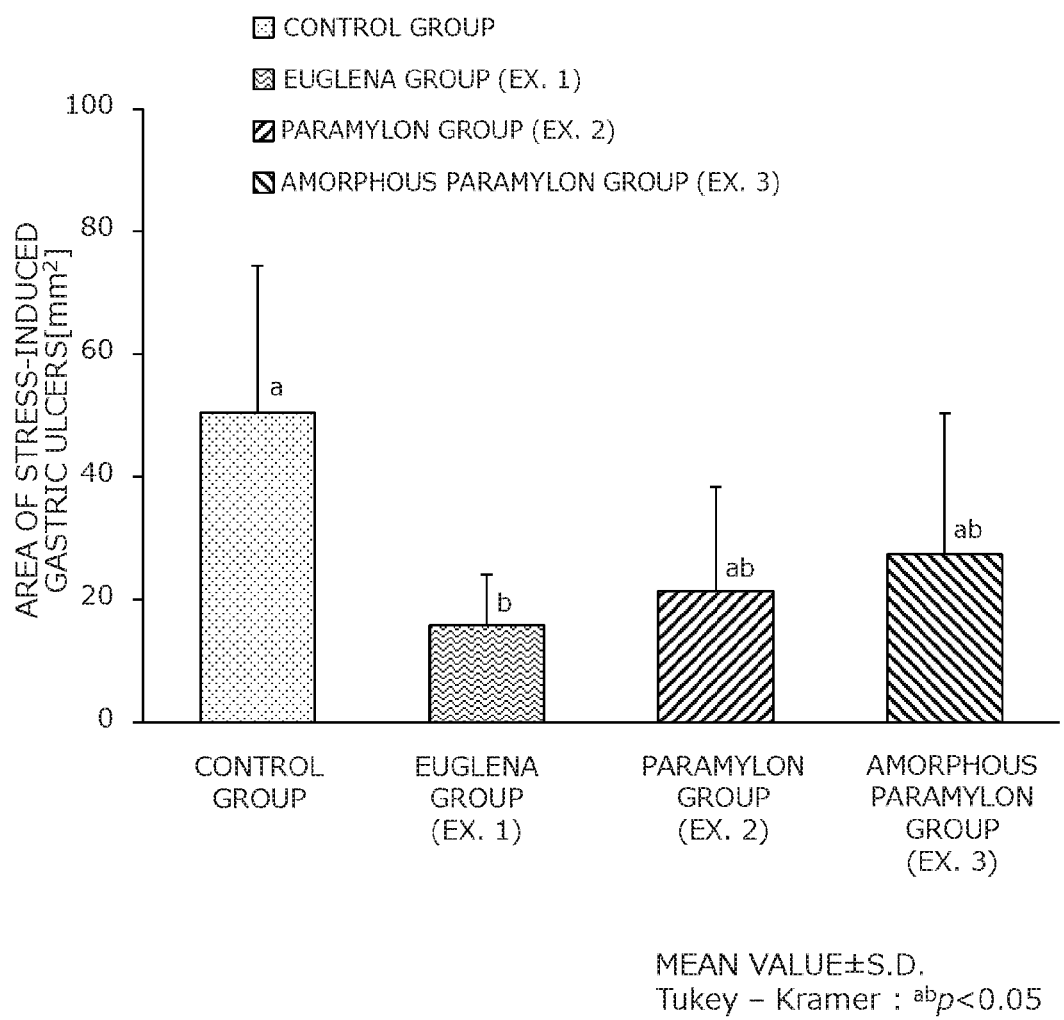
FIG. 4 is a graph illustrating measurement results of the areas of gastric ulcers in the respective groups in Test 1.

The photographs of gastric ulcers in representatives in each of the respective groups are illustrated in FIG. 3, and measurements of the areas of the ulcers are illustrated in FIG. 4.

As illustrated in FIG. 3, gastric ulcer portions (within ellipses) that became black due to blood stain were clearly observed in the control group, while gastric ulcer portions markedly shrunk in the Example 1-3 groups, compared with the control group. Particularly, gastric ulcer portions markedly shrunk in the Example 1 and 2 groups.

As illustrated in FIG. 4, the Example 1 group exhibited a significantly smaller area of gastric ulcers, compared with the control group (p<0.05 by Tukey-Kramer test). The Example 2 and 3 groups also tended to exhibit a smaller area. As illustrated in Table 3, the Example 1 and Example 2 groups exhibited an increased relative weight of duodenums. Thus, it is expected that the sample agents have a mechanism of action for protecting digestive organs against stress.

(Test 2)

In a similar water immersion stress test in rats, rats that were given the diets in admixture with the *Euglena* of Example 1, the paramylon of Example 2, or the amorphous paramylon of Example 3 as described in Table 1 and the rats that were given the control diet as described in Table 1 were immersed in water to chest level for 3.5 hours and dissected in the similar manner. Then, gastric mucosae of the rats of the control group and the Example 1-3 groups were removed and amplified using RT-PCR (using T100™ Thermal Cycler (BIO-RAD) System). The PCR products were analyzed on 2% agarose gel to examine the expression of iNOS (inducible nitric oxide synthase) and the expression of COX-2 (inducible cyclooxygenase).

As used herein, iNOS is a type of nitric oxide synthases (NOS), which produce nitric oxide from L-arginine and oxygen via an oxidation reaction. NOS are classified into neuronal NOS (type I, neuronal NOS, nNOS), endothelial NOS (type III, endothelial NOS, eNOS), and inducible NOS (type II, iNOS). iNOS is naturally bound to calmodulin and calcium and does not require increase in intracellular free calcium. iNOS is induced by cytokines and intracellular toxins and known to be involved in inflammatory conditions. Nitric oxide derived from iNOS has anti-virus and anti-bacterial effects in the host defense system and plays an important role in defense against infection, while the nitric oxide also leads to excessive inflammation (Med. Bull, Fukuoka Univ, 29(4), 247-255, 2002).

COX-2 is a type of cyclooxygenases (COX). COX are rate-limiting enzymes in biosynthesis of prostaglandin (PG) and have two isozymes: COX-1 and COX-2. COX-2, which is an inducible enzyme, is involved in conditions such as inflammation and oncogenesis and mainly exists in nuclear membranes in cells. COX expressed at a site of inflammation are mainly COX-2, and the expression of COX-2 at the site of inflammation induces synthesis of PG, which then leads to excessive inflammation.

Figure 5:
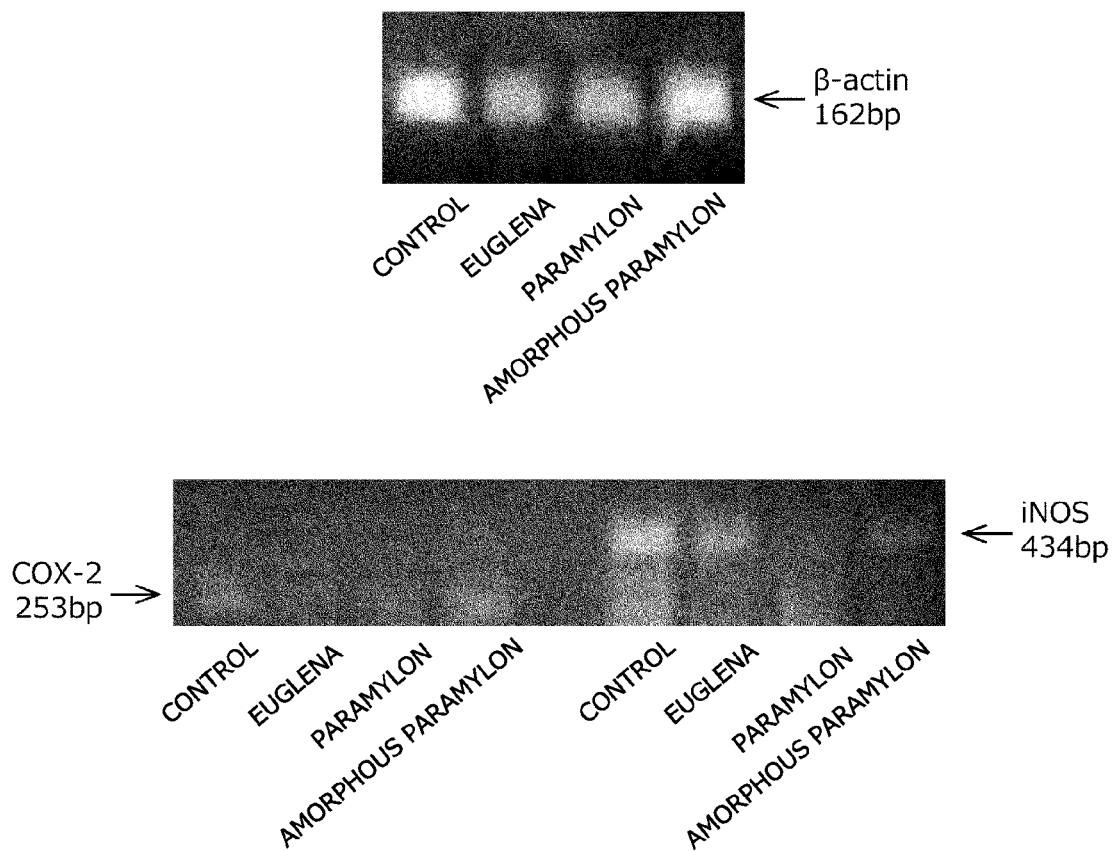
FIG. 5 shows photographs illustrating iNOS mRNA bands, COX-2 mRNA bands, and β-actin mRNA bands detected in Test 2.
Figure 6:
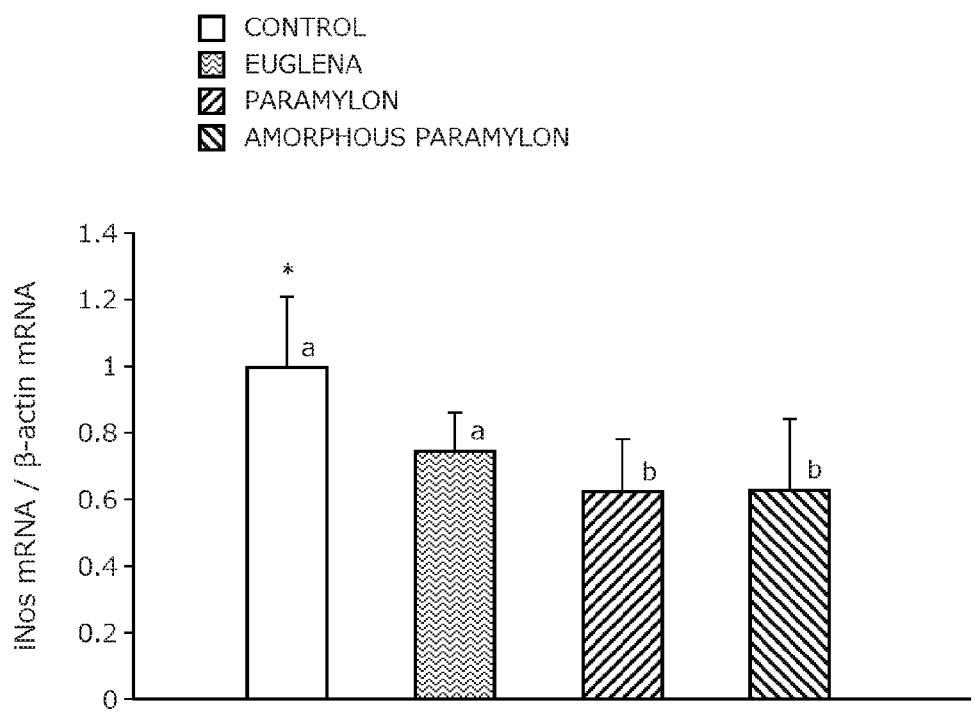
FIG. 6 is a graph illustrating iNOS/β-actin ratios in Test 2.
Figure 7:
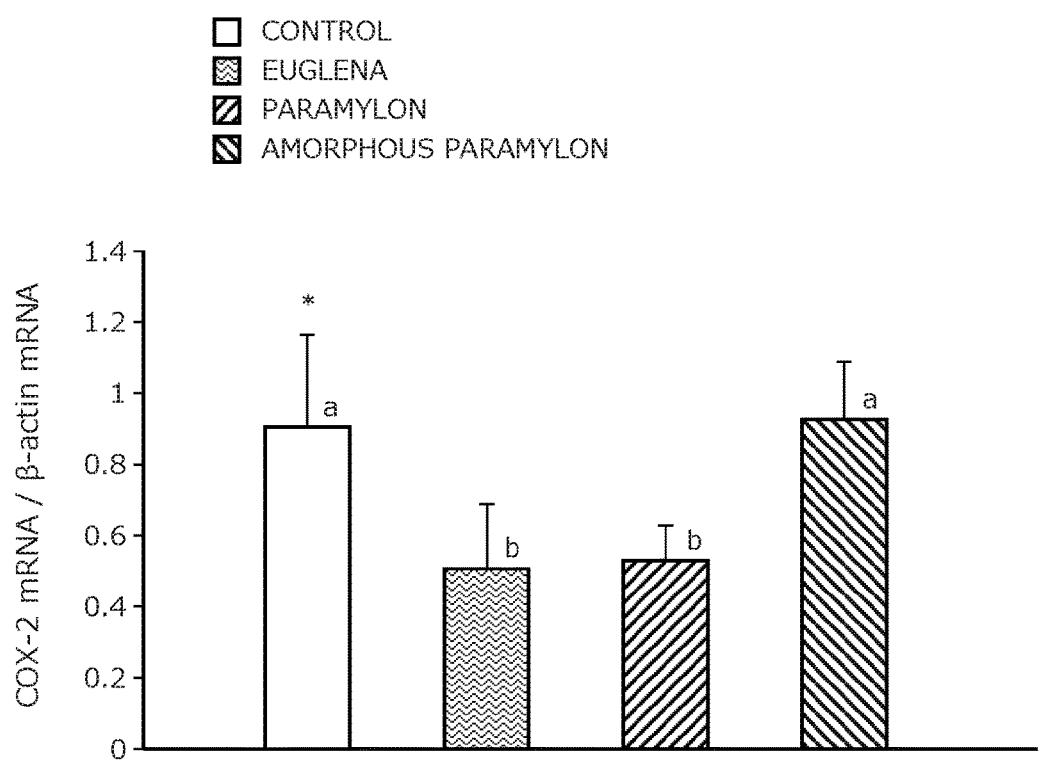
FIG. 7 is a graph illustrating COX-2/β-actin ratios in Test 2.

The analysis results are illustrated in FIGS. 5-7. As illustrated in FIG. 5, 434 bp, 253 bp, and 162 bp bands were seen, and iNOS mRNA, COX-2 mRNA, and β-actin mRNA were detected as PCR products. iNOS and COX-2 were normalized to β-actin. The figures illustrate relative indexes of the respective groups with the value of the control considered as 1.0.

FIG. 6 illustrates iNOS/β-actin, while FIG. 7 illustrates COX-2/β-actin. The results in FIG. 6 indicate that the *Euglena* group, the paramylon group, and the amorphous paramylon group exhibited inhibited expression of iNOS, compared with the control group. Especially, the paramylon group and the amorphous paramylon group exhibited a significant inhibition (p<0.05 by Turkey-Kramer test).

As illustrated in FIG. 7, the *Euglena* group and the paramylon group exhibited significantly inhibited expression of COX-2, compared with the control group (p<0.05 by Turkey-Kramer test).

Administration of *Euglena*, paramylon, or amorphous paramylon has been found to inhibit the expression of iNOS and COX-2, and thus it is expected that the administration reduced oxidative damage due to stress, thereby inhibiting a gastric ulcer.

Thus, it has been found that *Euglena*, paramylon, and amorphous paramylon provide anti-inflammatory effect through inhibition of expression of iNOS, which leads to excessive inflammation, and/or inhibition of expression of COX-2, which is a rate-limiting enzyme in biosynthesis of PG, which leads to excessive inflammation.

The *Euglena*, the paramylon, and the amorphous paramylon in the Examples have been shown to have the effect of inhibiting the expression of iNOS and/or the expression of COX-2. Thus, it has been found that the *Euglena*, the paramylon, and the amorphous paramylon in the Examples can be used as an iNOS expression inhibitor, a COX-2 expression inhibitor, and an anti-inflammatory agent.

The invention claimed is:

1. A method for treatment of a peptic ulcer, comprising: administering a composition comprising a *Euglena* as an active ingredient to a patient in need thereof.

2. The method according to claim 1, wherein said peptic ulcer is a peptic ulcer induced by psychological stress.

3. The method according to claim 1, wherein the peptic ulcer is a gastric ulcer.

* * * * *